C. M. SCHWARTZ

May 17, 1932. DIAPER Re. 18,468

Original Filed May 28, 1927

Inventor
Charles M. Schwartz
By his Attorney
Edwards & Henry

Reissued May 17, 1932

Re. 18,468

UNITED STATES PATENT OFFICE

CHARLES M. SCHWARTZ, OF PHILADELPHIA, PENNSYLVANIA, ASSIGNOR, BY MESNE ASSIGNMENTS, TO DIAPEX CORPORATION, OF NEW YORK, N. Y., A CORPORATION OF NEW YORK

DIAPER

Original No. 1,723,303, dated August 6, 1929, Serial No. 194,939, filed May 28, 1927. Application for reissue filed August 4, 1931. Serial No. 555,853.

The subject of this invention is a new article of manufacture, to wit, a one-use apparel garment for application to a child's body diaper-wise.

The invention, providing what may be termed a throw-away diaper, has the object of doing away with the ordinary diaper-cloth diapers, whenever possible, and particularly where the inconvenience and expense of repeated and frequent washings and dryings of the ordinary diapers, as well as the unsanitary aspects of this system, are appreciated.

The cost of each diaper used, and permanently discarded after one use, when the diaper is made according to the present invention, I have found to compare very favorably indeed with the cost of each use of an ordinary diaper, where a suitable stock of the latter are provided, and the laundering cost, the inconvenience due to rainy-weather interferences with the supply of dry diapers, etc., are all considered.

According to the present invention, the new one-use diaper is a freely flexible sheet structure including a plurality of dissimilar layers, these layers, especially if they are separate and distinct sheets, as is now deemed desirable, being preferably connected together so that they will during handling remain in their intended relative positions. By a freely flexible sheet structure is meant a sheet structure flexible about a child's limbs to be applied thereto diaper-wise as above stated; as contradistinguished from say, the comparative lack of flexibility of a common type of desk blotter made wholly of paper pulp and having the blotter-layer-proper facing a thin cardboard of relatively stiff paper layer.

According to the present invention, also, at least in its preferred form, the new diaper includes a plurality of layers of different degrees of softness, one which is a softer layer to be placed against the skin of the child and being of a water-absorbent material, as a soft layer like cotton batting. Another comparatively softer material may be employed for the softer layer, such, for instance, as a layer made of any fibrous material where the fibers are indiscriminately relatively extended, as contradistinguished from the intended distribution of such fibers found in sheet material formed as the result of weaving, knitting, or otherwise predeterminedly interlocking threads or preformed strands.

According to the present invention, also, at least in its preferred form, the new diaper, having a plurality of layers formed of fibrous elements as above, also includes a layer which is a water-proof layer.

The invention is most satisfactorily carried out, according to my experiments to date, by utilizing a different and distinct paper sheet for each of the different elements, and by providing a single water-proof paper underlying layer and a plurality of overlying water-absorbent paper layers.

Various other objects and advantages of the invention than those hereinabove mentioned will be specifically pointed out or will be apparent hereinafter in the course of the below detailed description of the forms of the invention shown, in the accompanying drawings, as preferred ones of the various possible embodiments of the invention; it being understood, naturally that such forms are merely illustrative of some of the many possible combinations and arrangements of parts well calculated to attain the objects of the invention, and hence said detailed description of such forms is not to be taken as at all defining or limiting the invention itself. That is to say, the scope of protection contemplated is of course to be taken from the appended claims, interpreted as broadly as is consistent with the prior art.

In said drawings.

Similar reference characters refer to similar parts throughout the several views of the drawings.

Figure 1:
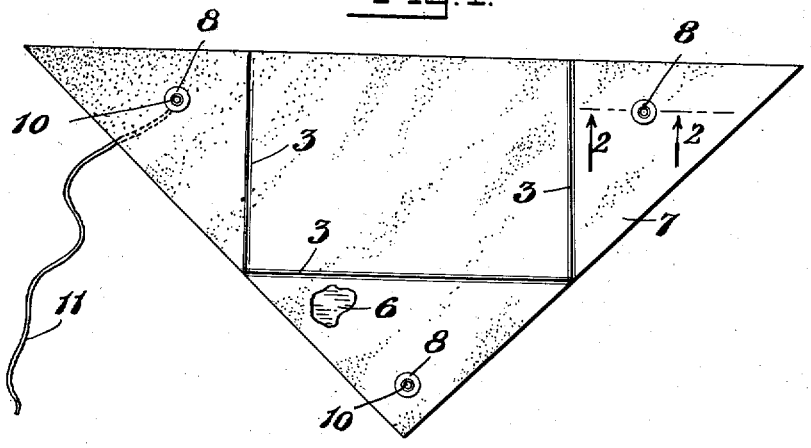
Fig. 1 is a plan view of one form, looking down on a softer layer.

Referring to the form of the invention shown in Fig. 1, the same is shown as comprising a superposed stack of triangular paper sheets, of which the underlying sheet 6 is ordinary comparatively thin brown paper, suitably waterproofed, as by paraffin wax, and the overlying sheets 7 are of thin soft and creped paper, such as is known in the paper art as Disband paper. As is well known, this type of paper last mentioned is fluffy, almost flocculent, resembles somewhat a very thin sheet of cotton batting, and is highly water-absorbent. While only three sheets 7 are illustrated for assisting clarity of illustration, any suitable number may be used, say eight or nine; together to constitute the water-absorbent layer of considerable softness as compared to the water-proof layer here provided by the single sheet 6.

It is desirable always in a diaper of any kind to avoid pins, even so-called safety pins. It is also most convenient in carrying out the present invention to secure the different layers, so as to maintain them in their intended locations during handling of the new diaper. Where, as just described, the layers are all formed as the result of providing a plurality of distinct sheets, the layers are desirably secured together at a plurality of spaced points. In the present case, the means for thus securing the sheets together form part of a means preferably incorporated, and forming a preferred feature of the invention, for use in holding the new diaper on the child in such a way that safety pins or the like for that purpose may be entirely avoided.

Figure 2:
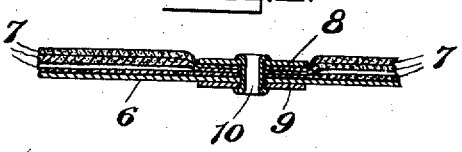
Fig. 2 is an enlarged detail, being a section taken on line 2—2 of Fig. 1.

As a preferred embodiment of the feature just referred to, a small cardboard piece as indicated at 8 is arranged on the top of the diaper, and an aligned similar piece 9 is laid underneath the diaper, at each of the points where the layers of the diaper are to be secured together, and then such securement is attained by applying an eyelet 10 and clinching the opposite ends of said eyelet against the pieces 8 and 9 which it has pierced, as shown most clearly in Fig. 2. This may compress the softer layer made up of the sheets 7, as indicated in Fig. 2; but this is no disadvantage, and indeed may be an advantage where such a fastener is applied to a part of the diaper which might be so located as to contact the child's body.

Figure 3:
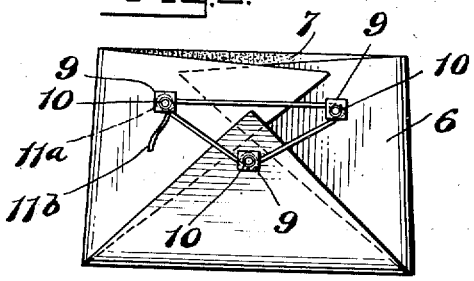
Fig. 3 is a front elevation of the form of Fig. 1, folded on the lines 3 of Fig. 1, and secured, as thus folded, in one possible way according to the invention, to be held diaper-wise as it would be held on a child's body.
Figure 4:
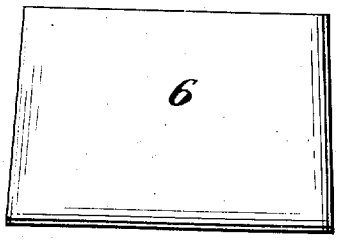
Fig. 4 is a rear elevation of the parts as arranged in Fig. 3.

The pieces 9, when the diaper is made as illustrated in Figs. 1 and 2, will appear as shown in Fig. 3 when the diaper is folded and applied to the child's limbs in the usual way. In the present case, the pieces 9 are indicated as square, and the pieces 8 are indicated as discs.

These discs 9 here form part of the means for securing the diaper in its folded condition on the child, the other element of said means being a flexible element, as an ordinary piece of string 11. This string may be anchored at one end by wrapping an end portion thereof about the shank of an eyelet and underneath a piece 9, and by then passing the string to another eyelet, then wrapping the string around the latter, and then passing the string to the third eyelet, and so on. In the present case, an end 11*a* of the string is assumed to be secured, say at the factory, about the eyelet 10 to the extreme left in Fig. 3; and the free length of the string is indicated as being by the nurse next passed around the eyelet 10 to the extreme right in Fig. 3, next around the eyelet 10 at the bottom in Fig. 3, and last passed around and locked to the first eyelet to leave the free end of the string dangling as indicated at 11*b* in Fig. 3.

Figure 5:
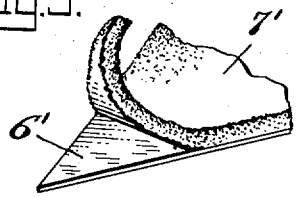
Fig. 5 is a fragmentary perspective view illustrating a different form of the invention.

Referring finally to Fig. 5, a form of the invention is shown wherein the underlying water-proof layer 6′ carries a single-mass water-absorbent layer 7′, as a layer of cotton batting.

Inasmuch as many changes could be made in the above constructions, and many apparently widely different embodiments of the invention could be made without departing from the scope thereof, it is intended that all matter contained in the above description or shown in the accompanying drawings shall be interpreted as illustrative and not in a limiting sense.

It is also to be understood that the language contained in the following claims is intended to cover all the generic and specific features of the invention herein described, and all statements of the scope of the invention which, as a matter of language, might be said to fall therebetween.

I claim:

1. As a new article of manufacture, a child's garment in the form of a diaper consisting of an outer sheet of impervious paper, a similarly shaped inner layer of soft absorbent paper, means for holding together said sheet and layer, such means comprising fastener members passing through the sheet and layer at points located near all of the pointed terminals of the garment, said fastening members providing means for securing the garment together about the wearer and a flexible securing member adapted to pass between and connect the fastening members.

2. A new article of manufacture comprising a child's diaper composed of an outer layer of impervious paper in substantially triangular form, an inner layer of absorbent material, fastening means for holding the layers together and for holding the garment in folded position about the wearer, said means comprising fastener members passing through the layers and providing spaced projections on the garment near each of the terminals thereon, and a flexible member adapted to pass between and connect each of said projections on the outside of the garment to hold the garment on the wearer.

3. A new article of manufacture comprising a child's diaper composed of an outer layer of impervious paper, an inner layer of absorbent material, fastening means for holding the layers together and for holding the garment in folded position about the wearer, said means comprising fastener members passing through the layers and providing spaced projections on the garment near the terminals thereon, and a flexible member adapted to pass between and connect said projections on the outside of the garment to hold the garment on the wearer.

4. A new article of manufacture comprising a triangular paper diaper formed of a plurality of layers of material and having several pointed terminals, buttons at spaced points thereon located adjacent to the pointed terminals and passing through the layers of the paper diaper for holding the layers together, a securing cord attached to one of said buttons and adapted to pass between and engage with the other buttons to act as a means for securing the garment about the wearer.

5. A new article of manufacture comprising a paper diaper formed of a plurality of layers of material and having several terminals, buttons at spaced points thereon located adjacent to the terminals and passing through the layers of the paper diaper for holding the layers together, a securing cord attached to one of said buttons and adapted to pass between and engage with the other buttons to act as a means for securing the garment about the wearer.

Signed at the city of New York, county of New York, State of New York, this 3 day of August, 1931.

CHAS. M. SCHWARTZ.